United States Patent
Lewis

(10) Patent No.: US 9,220,336 B1
(45) Date of Patent: Dec. 29, 2015

(54) BRUSH APPARATUS FOR INTERPROXIMAL CLEANING

(71) Applicant: Jacqueline D Lewis, Ocoee, FL (US)

(72) Inventor: Jacqueline D Lewis, Ocoee, FL (US)

(*) Notice: Subject to any disclaimer, the term of this patent is extended or adjusted under 35 U.S.C. 154(b) by 0 days.

(21) Appl. No.: 14/337,160

(22) Filed: Jul. 21, 2014

(51) Int. Cl.
*A46B 9/04* (2006.01)
*A46B 5/02* (2006.01)
*A46B 17/04* (2006.01)
*A61C 15/00* (2006.01)
*A46B 7/04* (2006.01)
*A46B 5/00* (2006.01)

(52) U.S. Cl.
CPC .............. *A46B 9/04* (2013.01); *A46B 5/0095* (2013.01); *A46B 5/02* (2013.01); *A46B 5/021* (2013.01); *A46B 7/046* (2013.01); *A46B 17/04* (2013.01); *A61C 15/00* (2013.01); *A46B 2200/108* (2013.01)

(58) Field of Classification Search
CPC ............ A61C 15/00; A46B 3/18; A46B 5/00; A46B 5/0095; A46B 5/02; A46B 5/021; A46B 7/04; A46B 7/046; A46B 9/04; A46B 17/04; A46B 2200/108
USPC .......... 15/143.1, 167.1, 176.2, 184, 194, 202, 15/206; 132/321, 329; 601/139, 141; D4/104, 111–113, 129, 131, 138; D28/65, 68
See application file for complete search history.

(56) References Cited

U.S. PATENT DOCUMENTS

| | | | | |
|---|---|---|---|---|
| 2,618,003 A | * | 11/1952 | Robey | 15/176.4 |
| 3,720,975 A | * | 3/1973 | Nelson | 15/167.1 |
| 4,691,404 A | * | 9/1987 | Tarrson et al. | 15/167.1 |
| 4,731,896 A | * | 3/1988 | de La Tour | 15/106 |
| 5,979,005 A | * | 11/1999 | Lecce | 15/167.1 |
| 6,973,932 B2 | | 12/2005 | Ko | |
| 8,356,380 B2 | | 1/2013 | Breitschmid | |
| 8,505,148 B2 | | 8/2013 | Atkin | |
| 8,528,147 B2 | | 9/2013 | Larsson et al. | |
| 8,567,000 B2 | | 10/2013 | Kubo | |
| 2010/0050358 A1 | | 3/2010 | Kim | |
| 2013/0000668 A1 | | 1/2013 | Madsen | |

FOREIGN PATENT DOCUMENTS

| | | | |
|---|---|---|---|
| JP | 9-47323 | * | 2/1997 |
| JP | 2009-50708 | * | 3/2009 |
| JP | 2009-240482 | * | 10/2009 |
| WO | 2006/061452 | * | 6/2006 |

* cited by examiner

*Primary Examiner* — Mark Spisich
(74) *Attorney, Agent, or Firm* — The Keys Law Firm PLLC

(57) ABSTRACT

An interproximal brush apparatus for dislodging and removing food particles and other debris is stuck between structures in a user's mouth comprises a curved handle defined by a rigid body having a hook shape, a bristle end defined by an elongated body having a plurality of bristles extending radially from its outer surface, and a docking member is defined by a rigid body connected to the shank of the curved handle on one end and the bristle on the other end. The curved handle enables the interproximal brush apparatus to be grasped and manipulated by a user with a single finger, while the bristle end is narrowly sized to enable it to slide between adjacent teeth of an individual, with the plurality of bristles contacting the teeth as the bristle end passes, making the bristle end operative to dislodge particles stuck in between teeth.

1 Claim, 1 Drawing Sheet

BRUSH APPARATUS FOR INTERPROXIMAL CLEANING

BACKGROUND OF THE INVENTION

1. Field of the Invention

This invention relates generally to oral hygiene instruments and, more particularly, to a brush apparatus adapted for interproximal teeth cleaning.

2. Description of the Prior Art

The use of conventional oral hygiene instruments, such as toothbrushes, floss, and tongue scrapers, to clean teeth, gums and a user's oral area of the body generally is well known. Such conventional oral hygiene instruments are commonly utilized to remove food particles, as well as to clean plaque and tartar, in and around teeth in order to maintain a healthy mouth. Despite widespread use of such conventional devices, a problem which still exists is that food particles that get stuck in between teeth, in braces, and even in bridges, are often difficult to remove conventional oral hygiene instruments. Thus, there remains a need for an interproximal brush apparatus which would enable a user to dislodge and remove food particles and other debris which is stuck in place in a user's mouth. It would be helpful if such an interproximal brush apparatus was sized to fit in between teeth, in braces, and even in bridges so as to reach areas inaccessible to conventional toothbrushes. It would be additionally desirable for such an interproximal brush apparatus to include a plurality of bristles to improve its efficacy in dislodging and removing food particles.

The Applicant's invention described herein provides for an interproximal brush apparatus adapted to glide between teeth, braces, bridges, and other dental structures in order to remove food particles. The primary components in Applicant's interproximal brush apparatus are a curved handle and a plurality of radial bristles. When in operation, the interproximal brush apparatus enables more effective cleaning between teeth by providing a rigid, bristled member to pass between and dislodge stuck material. As a result, many of the limitations imposed by prior art structures are removed.

SUMMARY OF THE INVENTION

An interproximal brush apparatus for dislodging and removing food particles and other debris is stuck between structures in a user's mouth. The interproximal brush apparatus comprises a curved handle defined by a rigid body having a hook shape, a bristle end defined by an elongated body having a plurality of bristles extending radially from its outer surface, and a docking member is defined as a rigid body connected to the shank of the curved handle on one end and the bristle on the other end, providing a docking means for connecting the two. The hook shape of the curved handle enables the interproximal brush apparatus to be grasped and manipulated by a user with a single finger, if desired, by simply wrapping the finger around the inner curve of the hook. As such, the curved handle provides a means for holding the interproximal brush apparatus. The bristle end is narrowly sized to enable it to slide between adjacent teeth of an individual, with the plurality of bristles contacting the teeth as the bristle end passes, making the bristle end operative to dislodge particles stuck in between teeth that would be unable to be moved by a flexible twine and providing a bristle means for removing particles between dental structures.

A removably attachable brush cap is additionally provided, operative to enclose the bristle end when the interproximal brush apparatus is not in use.

It is an object of this invention to provide an interproximal brush apparatus enables a user to dislodge and remove food particles and other debris which is stuck in place in a user's mouth.

It is another object of this invention to provide an interproximal brush apparatus sized to fit in between teeth, in braces, and even in bridges so as to reach areas inaccessible to conventional toothbrushes.

It is yet another object of this invention to provide an interproximal brush apparatus which includes a plurality of bristles to improve its efficacy in dislodging and removing food particles.

These and other objects will be apparent to one of skill in the art.

DETAILED DESCRIPTION OF THE INVENTION

Figure 1:
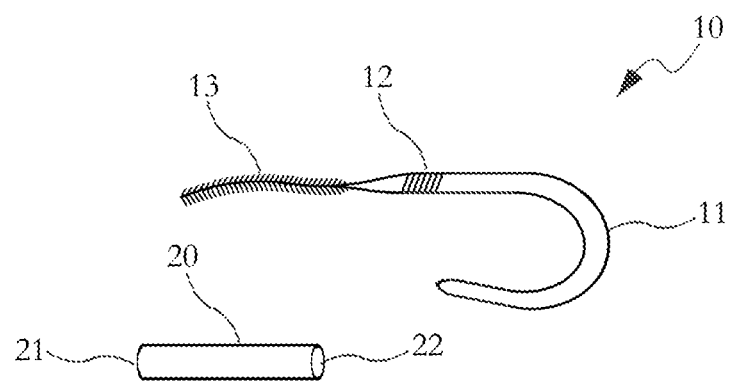
FIG. 1 is a side elevational view of an interproximal brush apparatus built in accordance with the present invention having its brush cap removed.

Referring now to the drawings and in particular FIG. 1, an interproximal brush apparatus 10 is shown having a curved handle 11, a docking member 12, and a bristle end 13. The curved handle 11 is a rigid body having a hook shape. The hook shape of the curved handle 11 enables the interproximal brush apparatus 10 to be grasped and manipulated by a user with a single finger, if desired, by simply wrapping the finger around the inner curve of the hook. It is understood, however, that the curved handle 11 may also be handled by a user with a plurality of fingers and/or digits.

The docking member 12 is defined by a rigid body connected to the shank of the curved handle 11 on one end and the bristle end 13 on the other end. In the preferred embodiment, outer surface of the docking member includes a plurality of threads to enable the attachment of a brush cap 20 structured to cover the bristle end 13.

The bristle end 13 is defined as an elongated body having a plurality of bristles extending radially from its outer surface. The bristle end 13 is narrowly sized to enable it to slide between adjacent teeth of an individual (or combination of other adjacent dental structures, including teeth, braces, and a bridges), with the plurality of bristles contacting the teeth (or other structure) as the bristle end 13 passes therethrough. Through its rigid spine and radial bristles, the bristle end 13 is able to dislodge particles stuck in between dental structures, such as teeth, that would be unable to be moved by a flexible twine.

The brush cap 20 is an elongated hollow body having a closed distal end 21 and an open proximal end 22, with the proximal end 22 additionally including a plurality of threads lining its inner surface. The brush cap 20 is removably attachable to the interproximal brush apparatus 10, with the proximal end 22 sliding over the bristle end 13, enclosing the bristle end 13 in its hollow body, and meeting the docking member 12 where the threads of the docking member 12 and of the proximal end 22 can engage to secure the brush cap 20 in place.

Figure 2:
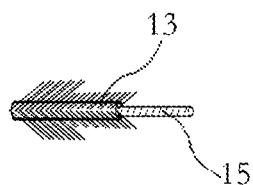
FIG. 2 is a side elevational view of the bristle end of an interproximal brush apparatus built in accordance with the present invention.

Referring now to FIG. 2, in one embodiment, the end of the docking member 12 to which the bristle end 13 attaches is hollow and includes a plurality of internal threads, while the end of the bristle end 13 which attaches to the docking member 12 includes a plurality of outer threads 15, enabling the bristle end 13 to be removably attached (screwed into and out of) the docking member 12.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An interproximal brush apparatus, comprising:
    a handle having a rigid body, wherein said handle has a proximal end and a distal end and is hook shaped such that both the proximal end and distal end are each oriented in the same direction;
    a bristle end having an outer surface and defined by an elongated body having a plurality of bristles extending radially from its outer surface, wherein said bristle end is connected to the proximal end of said handle through a docking member and narrowly sized to slide between adjacent teeth in a user's mouth;
    said docking member disposed between said handle and said bristle end and having an outer docking surface which includes a plurality of threads, wherein said bristle end is removably attached to said docking member; and
    a removably attachable brush cap having an inner cap surface, wherein said brush cap includes a proximal end having a plurality of threads disposed on the inner cap surface.

* * * * *